(12) United States Patent
Houston (10) Patent No.: US 7,556,594 B2
(45) Date of Patent: Jul. 7, 2009

(54) FITNESS DEVICE (76) Inventor: Vincent J. Houston, 33 Holland Pl., Hartsdale, NY (US) 10530

( * ) Notice: Subject to any disclaimer, the term of this patent is extended or adjusted under 35 U.S.C. 154(b) by 16 days.

(21) Appl. No.: 11/490,963

(22) Filed: Jul. 21, 2006

(65) Prior Publication Data
US 2007/0027480 A1   Feb. 1, 2007

Related U.S. Application Data

(63) Continuation-in-part of application No. 11/028,966, filed on Jan. 4, 2005, now abandoned.

(51) Int. Cl.
*A63B 26/00* (2006.01)
*A61F 5/00* (2006.01)

(52) U.S. Cl. .......... 482/142; 482/140; 482/907; 601/24; 601/25; 601/26; 606/242; 606/245

(58) Field of Classification Search .......... 606/242, 606/245; 482/131–137, 143, 907, 140, 142; 601/24–26

See application file for complete search history.

(56) References Cited

U.S. PATENT DOCUMENTS

| | | | | |
|---|---|---|---|---|
| 1,537,464 | A * | 5/1925 | Hummel, Jr. | 601/136 |
| 3,766,912 | A * | 10/1973 | Daniels | 606/242 |
| 4,696,512 | A * | 9/1987 | Burnett et al. | 297/68 |
| 4,782,715 | A * | 11/1988 | Chevance | 74/89.39 |
| 4,802,462 | A * | 2/1989 | Reiss et al. | 601/35 |
| 4,815,732 | A | 3/1989 | Mahvi | |
| 4,819,936 | A * | 4/1989 | Muller | 482/131 |
| 4,844,054 | A * | 7/1989 | Raemdonck | 601/27 |
| 4,844,453 | A | 7/1989 | Hestilow | |
| 4,876,929 | A | 10/1989 | Kozak | |
| 4,979,732 | A * | 12/1990 | Rushatz et al. | 482/148 |
| 5,256,126 | A * | 10/1993 | Grotstein | 482/142 |
| 5,437,609 | A * | 8/1995 | Leonard et al. | 601/91 |
| 5,468,216 | A * | 11/1995 | Johnson et al. | 601/24 |
| 5,567,202 | A * | 10/1996 | Hager | 482/131 |
| 5,728,048 | A * | 3/1998 | Hirschfeld | 601/24 |
| 5,913,759 | A * | 6/1999 | Bostrom | 482/142 |
| 5,971,901 | A * | 10/1999 | Shaw | 482/142 |
| 6,406,412 | B1 * | 6/2002 | Chen | 482/140 |
| 6,776,743 | B2 * | 8/2004 | Hur | 482/140 |
| 6,811,522 | B1 * | 11/2004 | McQuinn | 482/143 |
| 7,172,539 | B1 * | 2/2007 | Bythewood et al. | 482/140 |
| 2002/0149247 | A1 * | 10/2002 | Diffrient | 297/321 |
| 2003/0107250 | A1 * | 6/2003 | Staarink | 297/284.7 |
| 2006/0149317 | A1 * | 7/2006 | Freeman et al. | 606/242 |
| 2006/0161203 | A1 * | 7/2006 | Endara et al. | 606/241 |

* cited by examiner

*Primary Examiner*—Fenn C Mathew
*Assistant Examiner*—Andrew M Tecco
(74) *Attorney, Agent, or Firm*—Lackenbach Siegel LLP; Myron Greenspan (57) ABSTRACT

The Fitness Device comprises a back contacting member and a leg contacting member, with a pivotally mounted contacting member that is attached to said back contacting member. When driven by a motor or hand-operated power source, said pivotally mounted contacting member causes the position of said back contacting member relative to said leg contacting member to change, applying more or less pressure to the user's back (depending on the movement of said back contacting member) and thereby allowing the user's back to stretch relative to said leg contacting member.

9 Claims, 11 Drawing Sheets

FITNESS DEVICE

CROSS REFERENCE TO RELATED PATENT APPLICATIONS

This application is a continuation in part of U.S. patent application Ser. No. 11/028,966, filed on Jan. 4, 2005 now abandoned and entitled FITNESS DEVICE.

TECHNICAL FIELD

The present invention relates to a fitness device. More particularly, the present invention pertains to a fitness device for stretching the lower back and legs of a user.

STATEMENT REGARDING FEDERALLY SPONSORED RESEARCH OR DEVELOPMENT (Not Applicable)

BACKGROUND OF THE INVENTION

At least 100 million workdays are lost each year to lower back injuries at great cost to the economy. It has been estimated that workers compensation claims for back problems total billions of dollars each year. Exercise professionals know back pain and injury can largely be prevented through appropriate strengthening and stretching exercises.

Most athletes (both professional and recreational) know that in order to perform at their best level physically, it is necessary to warm up the body's muscles prior to performing an exercise. Also, to maintain muscle tone and flexibility, it is important to stretch one's muscles by exerting an elongating pulling force acting on the particular muscles being stretched. Typically, muscle stretching is performed by assuming a position in which a particular muscle group is elongated. This position is held for a period of time and then additional force is applied to further elongate the isolated muscle group.

When performing muscle stretching exercises, an athlete will typically concentrate stretching exercises that are designed to apply the elongating pulling force on the relatively larger muscle groups of the body, such as the muscle groups located in the legs and back. A common stretching procedure used to stretch the hamstring and lower back muscles is to stand straight up and then bend at the waist, while keeping the legs straight. The action of bending the torso at the waist exerts the desired pulling force on the muscles of the legs and back, and in particular, on the hamstring muscles. Since the hamstring muscles are one of the largest muscle groups of the body, used when performing many types of exercises and are commonly injured, it is very important to insure that the hamstring muscles of the legs receive an adequate stretching prior to, and after, exercising.

However, the traditional methods used for stretching the leg muscles and back muscles are inefficient, and place the athlete at a high risk of lower back injury. For example, when performing the above described stretching exercise where the torso is bent at the waist, the entire weight of the upper body is supported by the muscles of the lower back. This places a large strain on a group of muscles that tend to be weak and very tight in most individuals. Very often the back muscles are overloaded when a stretching exercise is performed, causing muscle fibers to tear, and resulting in debilitating pain and injury.

In order to provide a better stretch of the leg muscles and back muscles, another stretching method requires the athlete to sit with the back of the thighs flat on the ground with the toes of the feet pointing up. The athlete then reaches slowly forward with his hands towards his feet to bend the torso at the waist and perform the stretching exercise. A limber athlete will, in this position, be able to grab his feet with his hands and pull his chest towards his feet. In order to get a more consistent and more effective stretch, an assistant can apply an urging force to the back and shoulders of the athlete to urge the chest towards the feet. It is important for the assistant to exert enough of a force at an appropriate rate in order to obtain a good stretch of muscles, without causing pain or damage to the athlete. Typically, the athlete will communicate to the assistant how much pressure to apply and when to stop. In another method, which isolates the hamstring muscles from the lower back muscle (which is essential in some rehabilitation regimes), the individual lies on his back and places one leg straight up in the air. Typically a towel or band is placed around the foot so as to apply a force pulling the leg toward the chest.

With both of the described methods, not only is a force applied by the assistant, but also a counter force is applied by the athlete. This counter force is timed and released. As the counter force is released, the assistant is able to move further into the stretch. This stretching technique is referred to as PNF (proprio-neuro-facilitation) and is extensively used by rehabilitation professionals with excellent results. An assistant is very helpful when performing either of these stretching methods.

However, the traditional methods for stretching the legs and the back of an athlete without a trainer are inadequate. It is difficult for an athlete to exert enough of an urging force without resorting to dangerous bouncing motion. Also, even if an athlete is fortunate enough to have an assistant on hand to exert a consistent and adequate urging force, it is still difficult to obtain a good stretch, since the athlete must communicate with the assistant precisely when enough force is being applied, and how long to apply the force. If not enough force is applied, then the muscles do not receive an adequate stretch. If too much force is applied, then the athlete runs the risk of serious muscle and connecting tissue damage. Therefore, there is a need for a fitness device that an athlete can use alone for exerting and maintaining an appropriate force for both stretches described above. Since prevention and treatment for lower back and hamstring injuries involves obtaining increased flexibility or elongation of the muscles in this area, a device such as the present invention would have wide spread use among rehabilitation professionals as well as any commercial fitness facility.

SUMMARY OF THE INVENTION

The present invention is intended to provide a remedy. It is an object of the present invention to overcome the drawbacks of the traditional muscle stretching methods, and provide a simple fitness device that can be used by all individuals embarking on a fitness program. It is another object of the present invention to provide such a fitness device using a simple construction and common materials to keep manufacturing costs low. It is another object of the present invention to provide such a fitness device capable of indicating to the user the progress and improvement in the flexibility of the lower back and hamstring muscles of the user due to the use of the inventive fitness device.

U.S. Pat. No. 5,567,202 of Hager discloses a fitness device for use by a user having a back, legs, a torso, a waist, and a chest. A back contacting member is provided for contacting the back of the user. A leg contacting member is provided for contacting the legs of the user. An end of the back contacting member and an end of the leg contacting member are pivotally connected so that the back contacting member is pivotable relative to the leg contacting member. Thus, in an initial position, the back contacting member and the leg contacting member define a first angle. The user disposes himself so as to have his back contacting the back contacting member and his legs contacting the leg contacting member so that the torso and the legs of the user define substantially the first angle. A lever, operable by the user, is used to urge the back contacting member to pivot relative to the leg contacting member, and define a second angle. Thus, the back contacting member applies pressure to the back of the user to urge the chest toward the legs, so that the torso of the user bends at the waist, and the chest is urged toward the legs. The user takes hold of the lever, and pushes the lever forward with an appropriate force so that the legs and back of the user are properly stretched.

Also, in accordance with the Hager '202 patent, the position of the back contacting member relative to the position of the second contacting member could be locked, so that force is maintained against the back of the user to urge the chest toward the feet to obtain a good stretch to the leg muscles and back muscles, and in particular, of the hamstrings. This lock also allows the user to apply counter force in the back and leg contacting member. As counter force is increased, the back contacting member could be advanced against the counter force to maintain the increased muscle length obtained.

It is, however, somewhat inconvenient to operate the apparatus described in the Hager '202 patent. In particular, it is cumbersome and difficult for a user seated on the apparatus to effectively move the operating lever assembly that applies pressure to the back contacting member. There is, accordingly, a need for a more convenient way to cause the back contacting member to apply pressure to the user's back.

In the present invention, a pivotally mounted contacting member is connected to a shaft that is located underneath the leg contacting member that supports the user's legs. Extending the shaft in one direction causes the back contacting member to pitch towards the user, applying pressure to the user's back. Retracting the shaft in the opposite direction causes the back contacting member to pitch away from the user, removing pressure from the user's back. The shaft can be extended and retracted manually by means of a hand crank or a wheel or it can be extended and retracted under electrical power by connecting the shaft to an electric motor. Alternatively, the shaft can be threaded and can rotate, with a threaded nut fixed to the back contacting member causing the back contacting member to pitch accordingly. Another alternative is to connect the pivotally mounted contacting member to one ore more shafts that are located above the leg contacting member that supports the user's legs.

BRIEF DESCRIPTION OF THE DRAWINGS

Embodiments of the invention are described in detail below with reference to drawings which illustrates specific embodiments of the invention and in which.

BEST MODE FOR CARRYING OUT THE INVENTION

Figure 1:
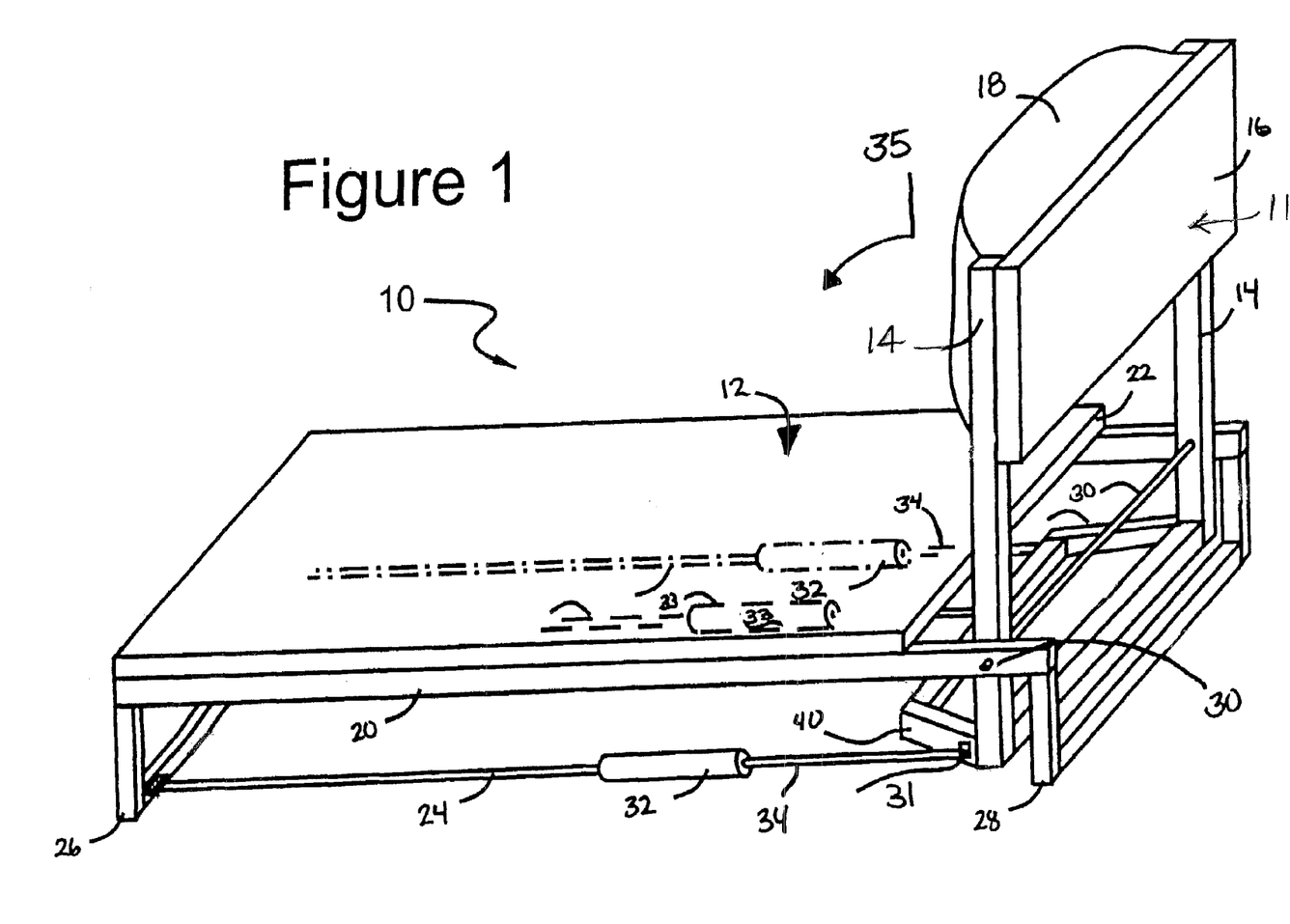
FIG. 1 is a perspective view of an embodiment of the fitness device in accordance with the present invention.

FIG. 1 shows a perspective view of an embodiment of the fitness device in accordance with the present invention. The inventive fitness device 10 has been designed so that a user can obtain a safe and effective stretch to particular muscles (back and legs), without requiring the help of an assistant. The inventive fitness device allows a user to apply and maintain an appropriate urging force for driving his chest toward his feet so that the torso bends at the waist, and the back and leg muscles are adequately stretched, and also to apply a counter force to produce a greater elongation of the isolated muscle.

Figure 1A:
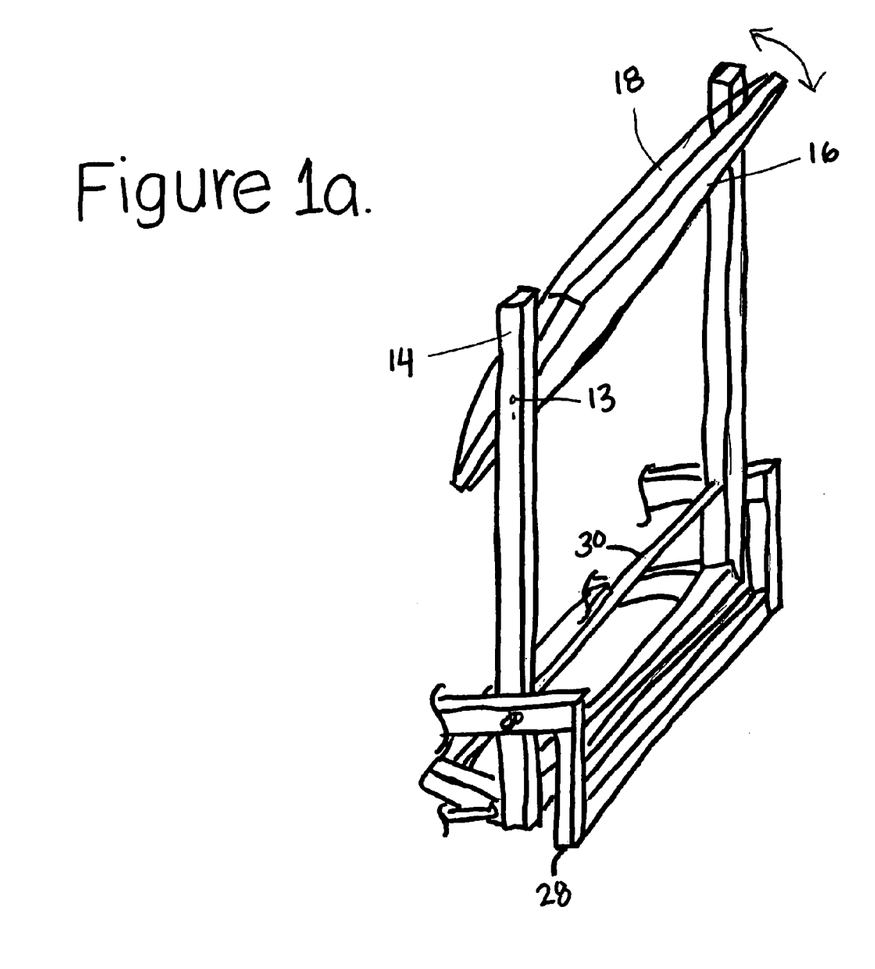
FIG. 1a is a perspective view of a pivotable backrest in accordance with one embodiment of the present invention.

As shown in FIG. 1, a back contacting member 11 is provided for contacting at least a portion of the back of a user seated on the leg contacting member 12. The back contacting member 11 comprises a metal (e.g. steel) back frame 14 which supports a durable contacting surface, such as panels of wood 16 covered on one side by a padded vinyl contacting pillow 18. As shown in FIG. 1a, the back panel 16 may be pivotably mounted to back frame 14 by screws, pins, or similar means at pivot point 13. Doing so allows back panel 16 to pivot relative to back frame 14 when the invention is in use. Contacting pillow 18 is secured to the back frame 14 and back panel 16 by screws, or other securing devices. Leg contacting member 12 comprises a seat frame 20, which supports a contacting bed member 22 that is fixed to steel seat frame 20 by screws, or other securing devices.

The back contacting member 11 and/or the leg contacting bed member 12 may be constructed of solid sheets of a suitable material, such as plastic, wood, or metal. However, in accordance with the embodiment shown in FIG. 1, an easy-to-manufacture and light-weight construction is obtained for the inventive fitness device. The back frame 14 and the seat frame 20 may be constructed from metal tubing, plastic tubing, or wood. Preferably, aluminum tubing is used. A metal front frame support 26 and a rear frame support 28 are of a suitable size to elevate the back frame 14 and seat frame 20 above the floor so that the foot 31 of back contacting member 11 clears the floor and can pivot freely. The second contacting member 12 is at any height convenient for users to position themselves on the apparatus. The back contacting member 11 is pivotally connected to the second contacting member 12 by pivot shaft 30.

In use, two 32 or one motor 33 (which is centrally positioned) are connected to the front frame support 26, each by a connecting shaft 24. Laterally movable shaft 34 runs from each motor to the back contacting member 11 at a point below the pivot shaft 30 of the back contacting member 11.

As the motors 32 operate each laterally movable shaft 34 either advances or retracts depending on the direction of motor rotation. As it advances, shaft 34 causes the upper portion of back contacting member 11 to pivot forward in the direction of arrow 35 relative to the second contacting member 12 so that the torso of the seated user bends at the waist and the user's chest is urged towards the user's legs. The user thereby stretches the muscles of the back and legs. As each retracts, laterally movable shaft 34 causes the back contacting member 11 to pivot back relative to the second contacting member 12, allowing a seated user to move the user's chest away from his or her legs.

The motors 32 and laterally movable shafts 34 work together with one another or motor-and-shaft assembly may be used.

Figure 2:
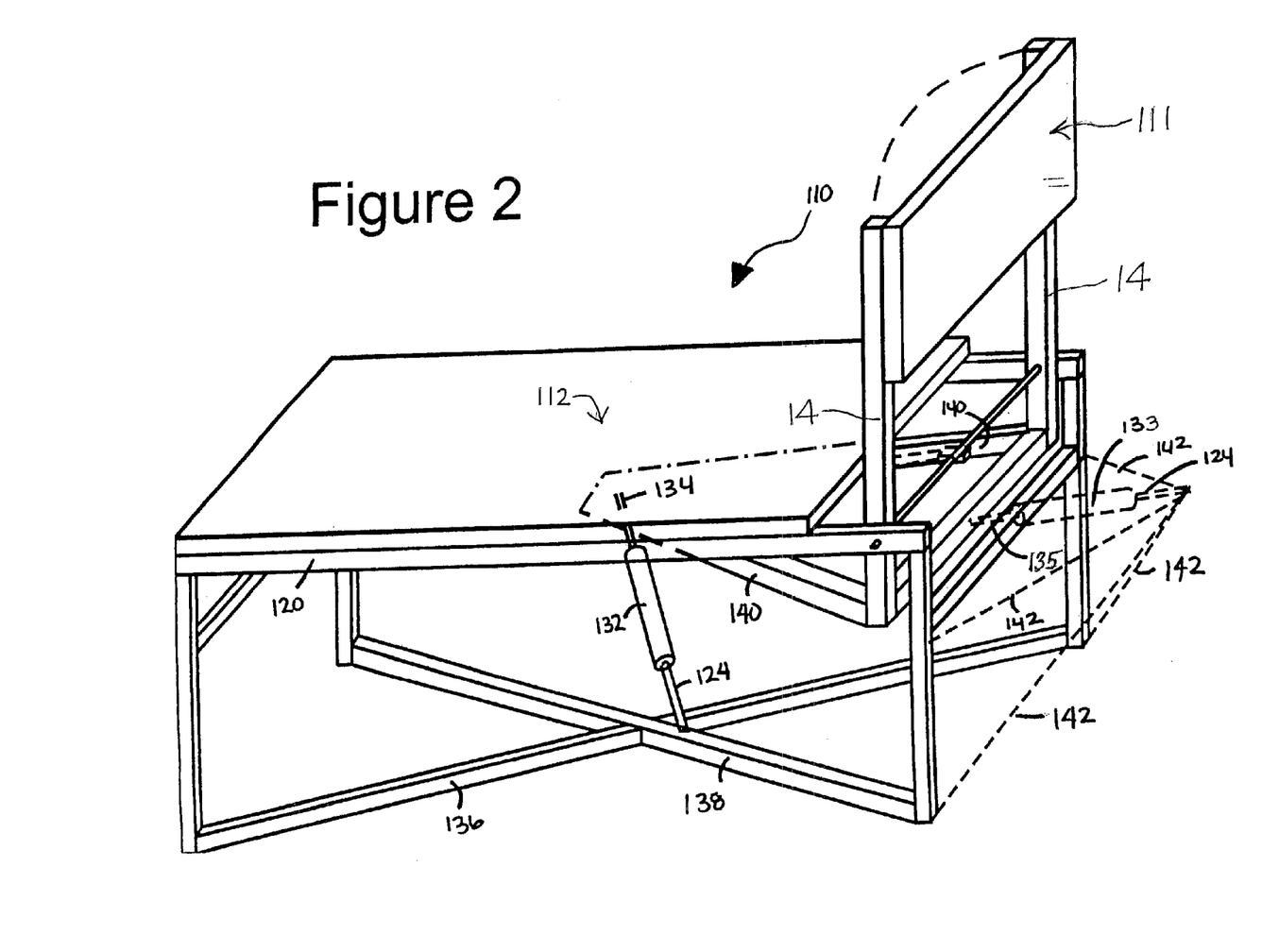
FIG. 2 is a perspective view of an alternative embodiment of the fitness device in accordance with the present invention.

FIG. 2 shows an alternative embodiment 110 of the inventive fitness device, in which the connecting shaft 124 is fixed to cross braces 136, 138 that run cross-ways, front to back, from opposite corners of the apparatus underneath the seat frame 120.

A lever arm 140 is attached to the bottom of back frame 14 and acts as a lever to multiply the force applied to the lower part of back contacting member 111.

Connecting shaft 124 supports motor 132 that is connected to the lever arm 140 by laterally movable shaft 134. As the motor 132 turns, movable shaft 134 either advances or retracts, depending on the direction of motor rotation. As it advances, laterally movable shaft 134 causes the lever arm 140 to move up towards the bottom of the leg contacting member 112. This causes the back contacting member 111 to pivot back relative to the second contacting member 112, allowing a seated user to move the user's chest away from his or her legs.

As it retracts, movable shaft 134 causes the lever arm 140 to move down towards the cross braces 136 and 138. This causes the back contacting member 111 to pivot forward relative to the leg contacting member 112 so that the torso of a seated user bends at the waist, and a user's chest is urged towards the user's legs.

Alternatively, as shown in the dashed lines on FIG. 2, the motor 132 may be attached by shaft 124 to a motor suspension frame 142 located at the rear of the fitness device. Laterally movable shaft 135 runs from motor 133 to the back contacting member 111. As the motor 133 turns, laterally movable shaft 135 either advances or retracts, depending on the direction of rotation. As it advances, laterally movable shaft 135 causes the back contacting member 111 to pivot back relative to the second contacting member 112, allowing a seated user to move the user's chest away from his or her legs. As it retracts, laterally movable shaft 135 causes the back contacting member 111 to pivot forward relative to the leg contacting member 112 so that the torso of the seated user bends at the waist, and the user's chest is urged towards the user's legs.

Figures 3, 4:
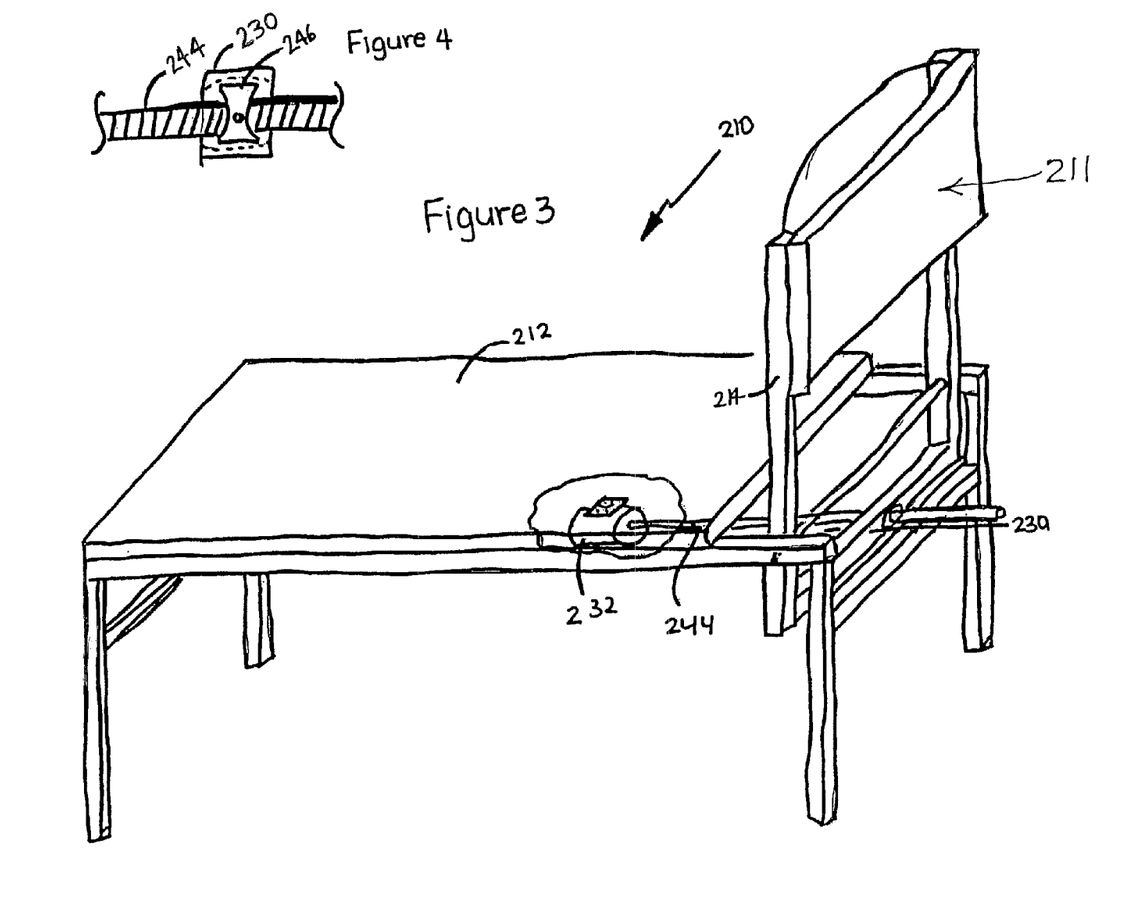
FIG. 3 is a perspective view of another embodiment of the fitness device in accordance with the present invention.
FIG. 4 is a cutaway side view of a threaded shaft as it passes through the threaded nut and a portion of the back contacting member, in accordance with one embodiment of the present invention.

FIG. 3 shows an alternative embodiment 210 of the inventive fitness device. Motor 232 is mounted to the underside of second contacting member 212. Threaded shaft 244 runs from motor 232 to a pivotable threaded nut 246 (FIG. 4) located at a suitable lower member 230 of the frame 214 of the back contacting member 211. As the motor 232 turns, the threaded shaft 244 turns as well, and pivotable threaded nut 246 (FIG. 4) moves either closer to or further away from motor 232, depending on the motor's direction of rotation.

FIG. 4 shows a cutaway detail of the relative position of pivotable threaded nut 246 within the first contacting member 211.

As pivotable nut 246 moves closer to motor 232, the upper portion of back contacting member 211 pivots away from second contacting member 212, allowing a seated user to move the user's chest away from his or her legs. As pivotable threaded nut 246 moves away from motor 232, the upper portion of back contacting member 211 pivots toward second contacting member 212 so that the torso of the seated user bends at the waist, and the user's chest is urged towards the user's legs.

Figure 5:
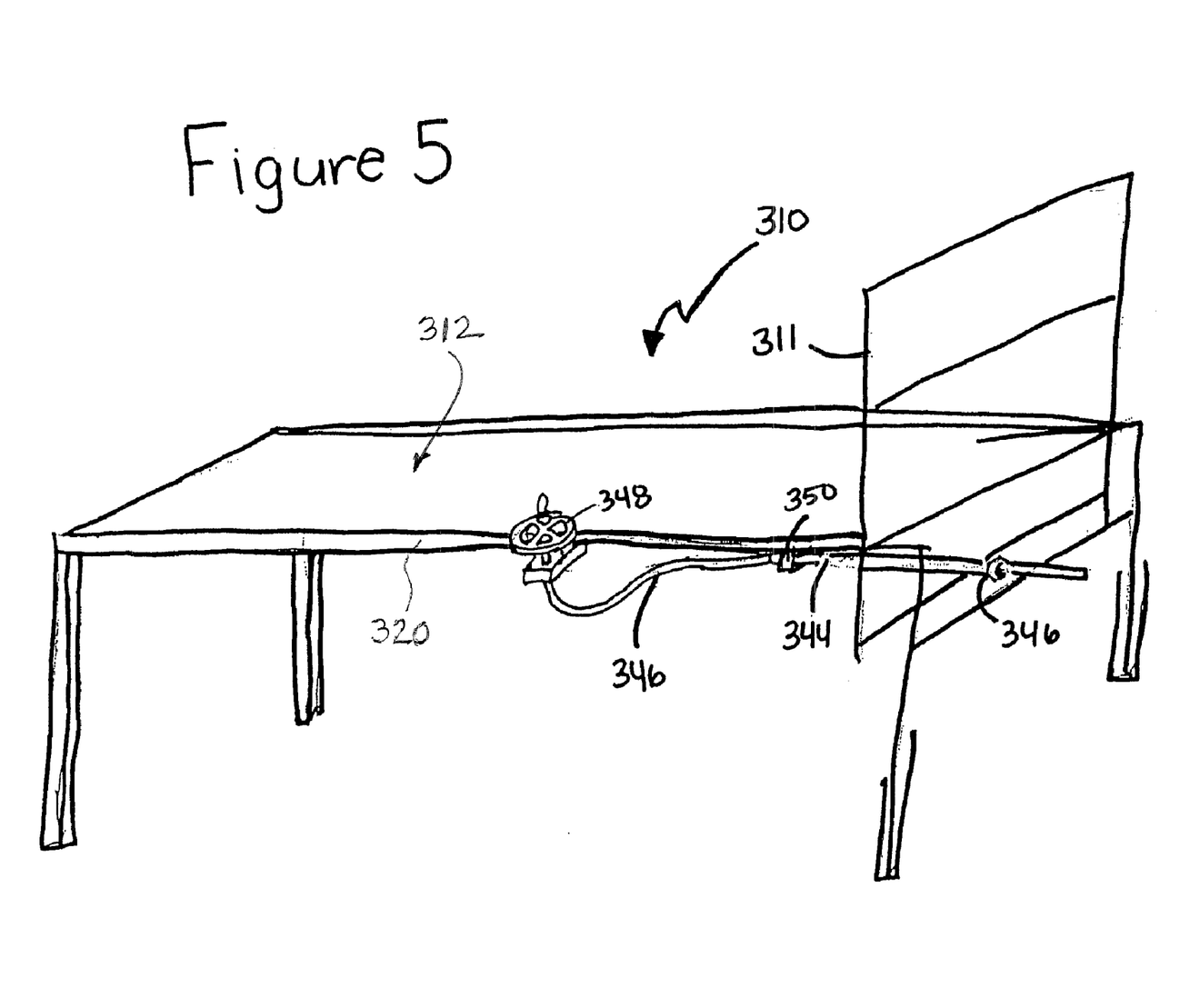
FIG. 5 is a perspective view of another embodiment of the fitness device in accordance with the present invention.

FIG. 5 shows an alternative embodiment 310 of the inventive fitness device similar to that of the FIG. 2 embodiment, in which a threaded shaft 344 is driven by flexible drive shaft 346. Flexible drive shaft 346 is powered by hand crank 348, which is mounted to the side of seat frame 320 at a point convenient for the user to access. Drive shaft 346 may be of a type known in the art as exemplified by that disclosed in U.S. Pat. No. 4,876,929 of Kozak and comprising a number of counter wound devices forming a cable housed in flexible gooseneck housing. Threaded shaft 344 is fixed in place by pillow block 350, which is fixed to the underside of second contacting member 312. Turning hand crank 348 in one direction or the other causes the back contacting member 311 to pivot one way or another, in the manner described with respect to FIG. 3.

Figure 6:
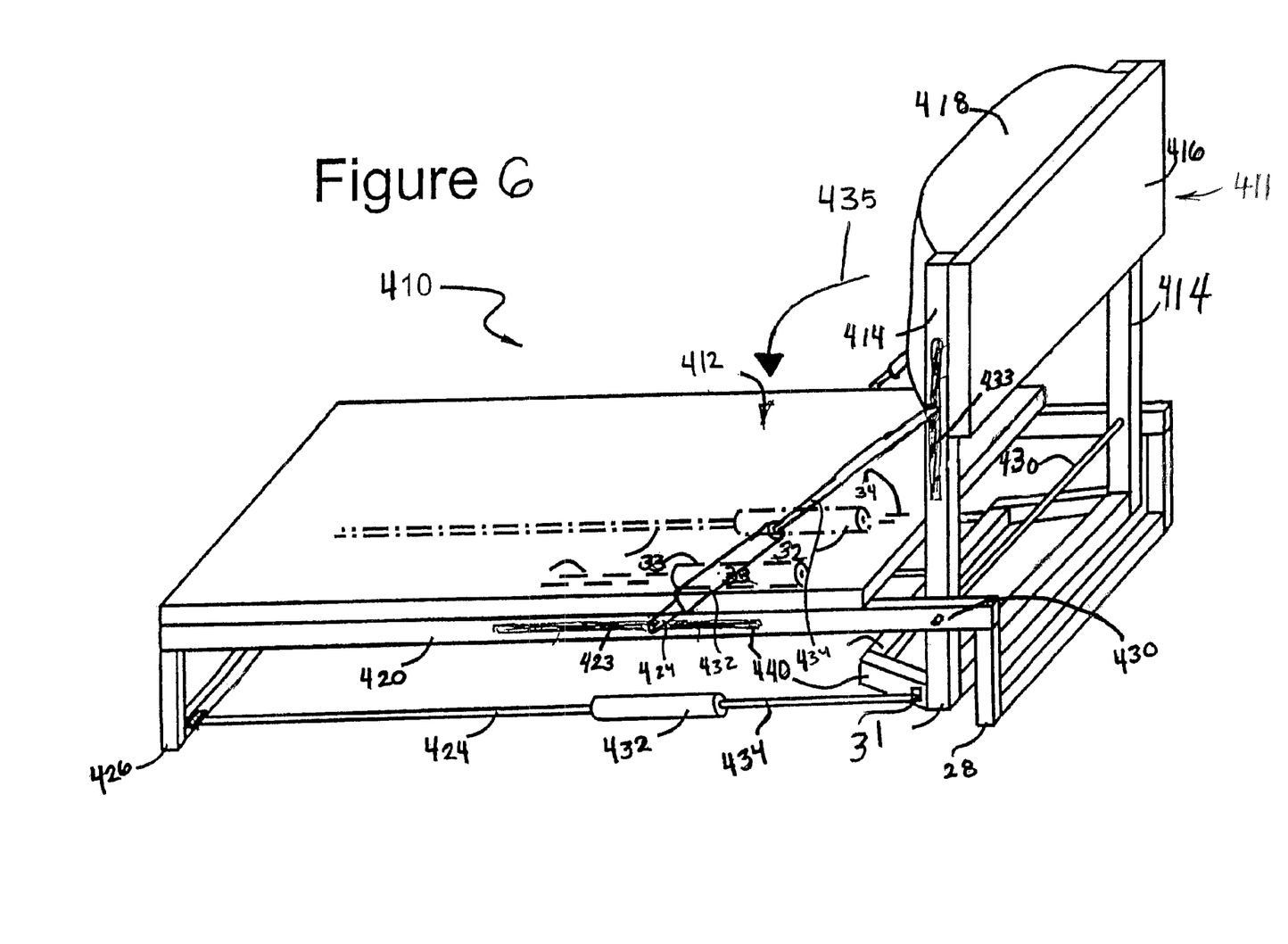
FIG. 6 is a perspective view of another embodiment of the fitness device in accordance with the present invention.

FIG. 6 shows an alternative embodiment 410 of the inventive fitness device similar to that of the FIG. 1 embodiment. In this case, each motor 432 is connected to the seat frame 420 by a connecting shaft 424. A laterally movable shaft 434 runs from each motor to the back contacting member 411 at a point above the pivot shaft 430 of the back contacting member 411. The connecting shaft 424 may also connect to the seat frame 420 by means of a wing nut or similar device riding inside of channel 423 so as to provide a wide range of adjustability. Alternatively, a series of fixed mounting holes could be used. Moving the point at which connecting shaft 424 connects to the frame 420 will vary the initial angle at which back member 411 begins to operate. Similarly, the laterally movable shaft 434 may contact back contacting member 411 by means of a similarly adjustable wing nut or other such device riding inside channel 433. Doing so will also vary the initial angle at which back frame member 414 begins to operate. Here, as in FIG. 1, as each motor 432 operates, each laterally movable shaft 434 either advances or retracts depending on the direction of motor rotation. As it advances, each laterally movable shaft 434 causes the upper portion of back contacting member 411 and contacting surface 416 to pivot back relative to the second contacting member 412, allowing a seated user to move the user's chest away from his or her legs. As each laterally movable shaft 434 retracts, it causes the upper portion of back contacting member 411 to pivot forward in the direction of arrow 435 relative to the second contacting member 412 so that the torso of the seated user bends at the waist and the user's chest s urged forwards the user's legs.

Figure 7:
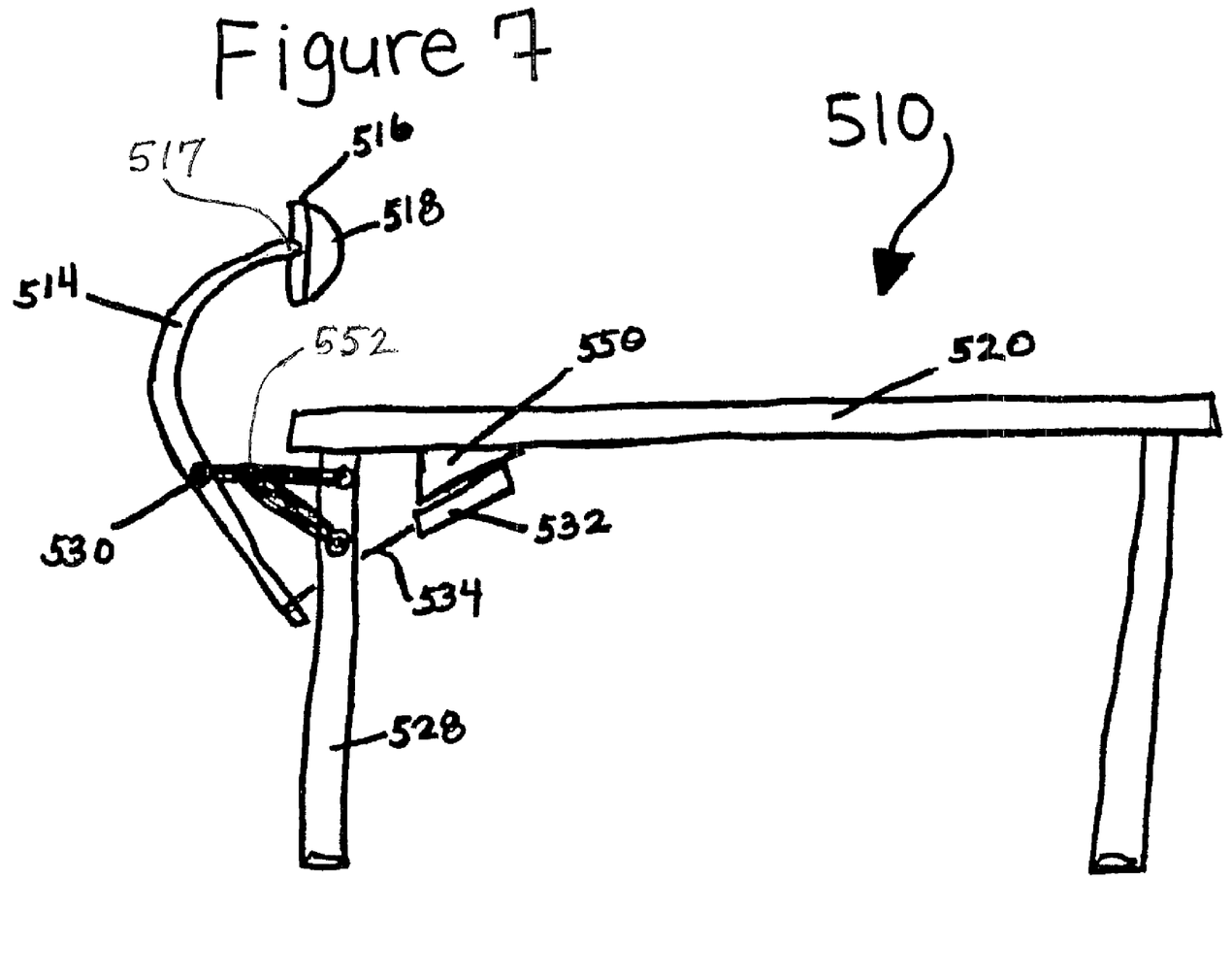
FIG. 7 is a perspective view of another embodiment of the fitness device in accordance with the present invention.

FIG. 7 shows an alternative embodiment 510 of this inventive fitness device designed to be attached to an existing table or base. In this case, back frame 514 is attached at pivot point 530 to a mounting bracket 552. Mounting bracket 552 is designed to support back frame 514 and to attach to existing table legs 528, existing table top 520, or both. Drive motor mounting block 550 attaches to the underside of existing table top 520, and is ideally structured so that when motor 532 is attached, motor 532 is optimally positioned to deliver the greatest amount of force to back frame 514.

Here, as in other embodiments, operation of motor 532 in one direction causes laterally movable shaft 534 to move back frame 514 in one direction or the other. Reversing motor 532 reverses the direction of movement of back frame 514.

Depending on the direction of movement of back frame 514, the user's torso will either be pushed towards or moved away from the user's legs.

Figure 7A:
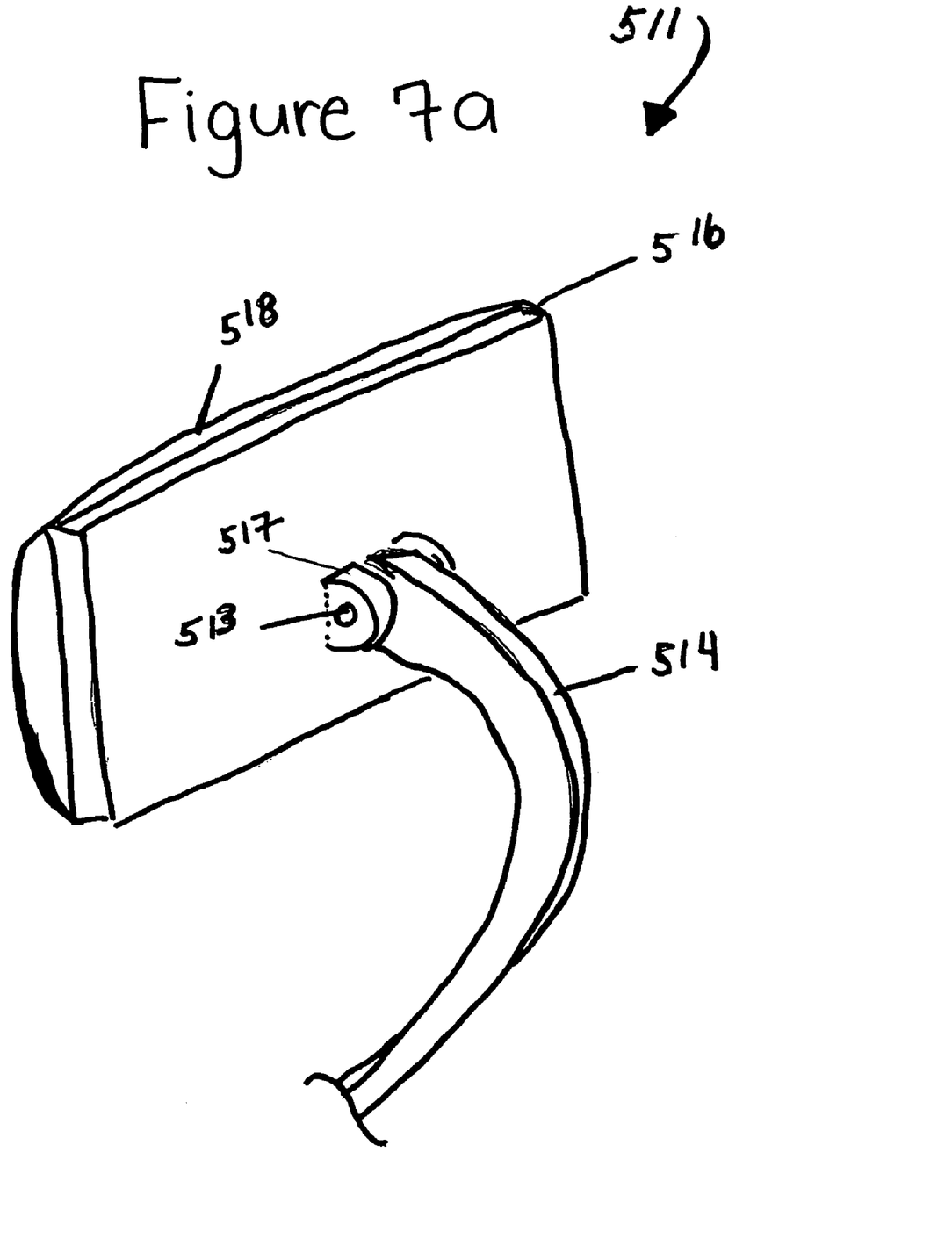
FIG. 7a is a perspective view of a pivotable backrest in accordance with one embodiment of the present invention.

FIG. 7a shows an alternative mounting method 511 for back panel 516. In this embodiment, the back panel 516 may be pivotably mounted to back frame 514 by screws, pins, or similar means at pivot point 513, through bracket 517. Doing so allows back panel 516 and back pillow 518 to pivot relative to back frame 514 when the invention is in use.

Figure 8:
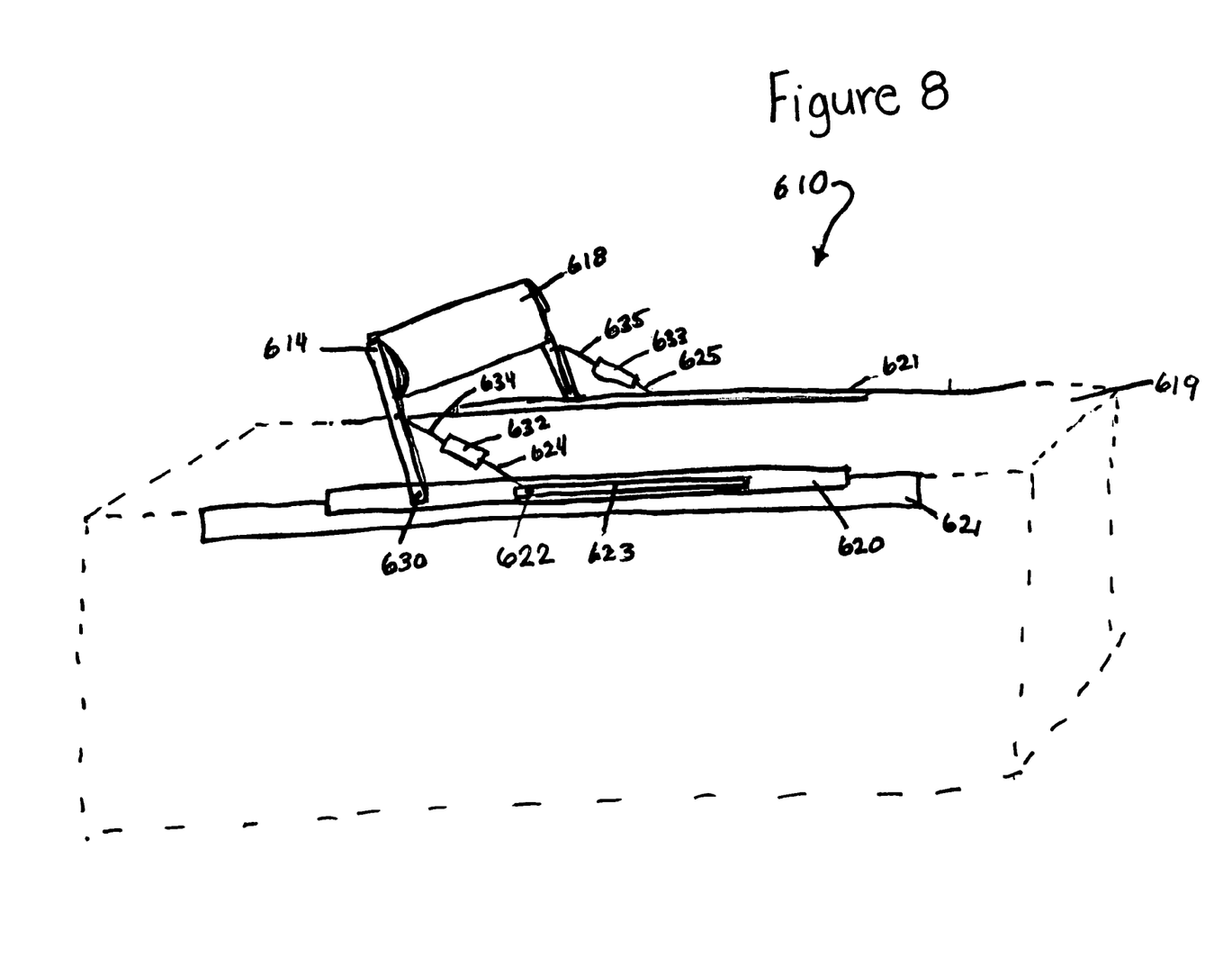
FIG. 8 is a perspective view of another embodiment of the fitness device in accordance with the present invention.

FIG. 8 shows an alternative embodiment 610 of this inventive device designed to be attached to an existing table or base. In this case, guide rails 621 are attached to the sides of the existing table or base 619. Support rails 620 attach to guide rails 621 by means of set screws, clamps, or similar hardware. Varying the position of the support rails 620 along the guide rails 621 allows the user to move the device forward or back along the guide rails 621.

Here, back frame 614 is attached on either side to support rails 620, 621 at pivot point 630. A connecting shaft 624, 625 attaches to support rails 620 and supports one motor 632, 633 on either side of the table or base. Each motor 632, 633 is connected to back frame 614 by a laterally-movable shaft 634, 635. Looking only at the left-hand side of the invention, the connecting shaft 624 may also connect to support rail 620 at point 622 which may comprise a wing nut or similar device riding inside of channel 623 so as to provide a wide range of adjustability. Alternatively, a series of fixed mounting holes could be used. Moving the point at which the connecting shaft 624 is fastened to the frame 620 will vary the initial angle at which back frame 614 begins to operate. The right-hand side connecting shaft is mounted in the same fashion as described above. As motor 632 turns, the laterally-movable shaft 634 either advances or retracts, depending on the direction of motor rotation. As it advances, laterally movable shaft 634 causes back frame 614 to move away from the user. As it retracts, laterally-movable shaft 634 causes back frame 614 to move towards the user. Here, too, back panel 618 may be pivotably mounted to back frame 614 in a fashion similar to that shown in FIG. 1a.

Figure 9:
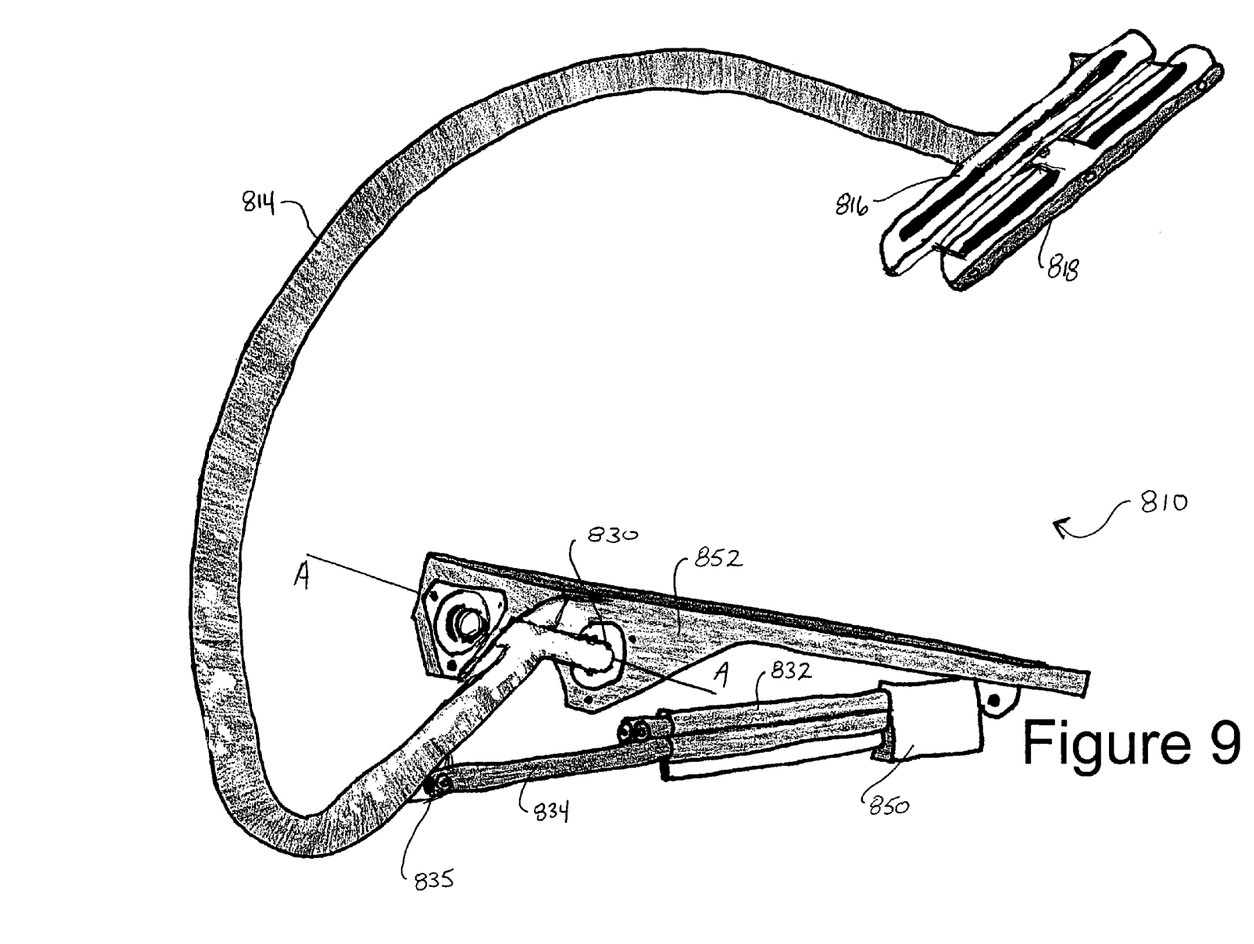
FIG. 9 is a perspective view of another embodiment of the fitness device in accordance with the present invention.
Figure 10:
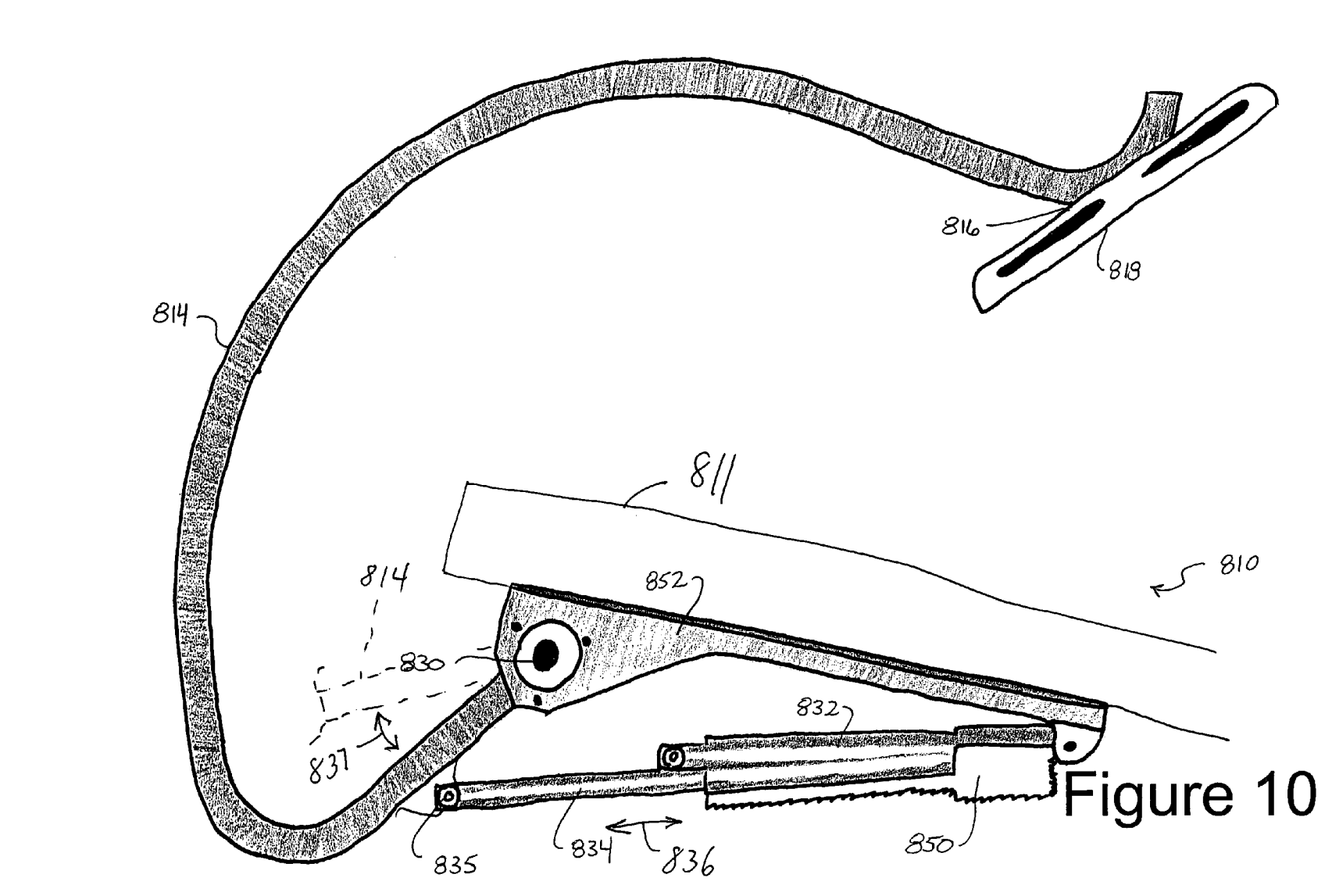
FIG. 10 is a side view of the fitness device shown in FIG. 9.

FIGS. 9 and 10 show an alternate embodiment 810 of this inventive fitness device designed to be attached to an existing table or base (not shown). It is contemplated that fitness device 810 may be specifically manufactured for assembly with specific structures, such as a table 811, base, etc., or also may be integrally fabricated with the original manufacture of a structure.

A back frame 814 is attached at a pivot point 830, which lies on axis A (shown in FIG. 9), to a mounting bracket 852. Axis A is defined by the connection of back frame 814 and mounting bracket 852 such that back frame 814 pivots thereabout. Mounting bracket 852 is designed to support back frame 814 (which may be made of any rigid or flexible material such as stainless steel or a strong plastic material) for pivotal movement about pivot point 830. Such pivotal movement provides movement of back frame 814 along an arcuate path in an advantageous configuration that facilitates safe and effective stretching of a user's muscles, in accordance with the principles of the present disclosure.

Back frame 814 has an arcuate configuration. This advantageous design facilitates movement of back frame 814 about the table relative to pivot point 830, which can accommodate several table end variations. It is contemplated that back frame 814 may have various radii of curvature to form the arcuate design. It is envisioned that pivot point 830, which lies on Axis A, is adjacent and/or closely aligned to the pivot point of user's hip to avoid undesirable longitudinal movement of a portion of fitness device 810 that engages a user such as a pad discussed below, during use. It is contemplated that pivot point 830 may include a rotatable bearing structure to facilitate movement of back frame 814 relative to mounting bracket 852. Such bearing structure may be mounted with back frame 814 or mounting bracket 852.

Mounting bracket 852 is configured for mounting with a surface of the table or base. It is envisioned that mounting bracket 852 may be attached to a planar surface, although mounting bracket 852 may be configured for attachment with surfaces having other configurations, such as arcuate, cornered, angled, etc. Mounting bracket 852 is attached to the underside of a tabletop by various methods such as adhesive, mechanical, etc.

A motor 832 and motor mounting block 850 are attached to mounting bracket 852. It is contemplated that motor 832 is positioned with the underside of the tabletop to deliver the greatest amount of force to back frame 814. Similar to the embodiments discussed above, operation of motor 832 in one direction causes a laterally movable shaft 834 to move back frame 814 in one direction or the other. Reversing motor 832 reverses the direction of movement of back frame 814. Depending on the direction of movement of back frame 814, the user's torso will either be pushed towards or move away from the user's legs.

Moveable shaft 834 extends from motor 832 to a distal end 835 and moves in the directions indicated by arrows 836. This results in movement of pad 818 and back frame 814 in the directions of arrows 837. Distal end 835 engages back frame 814 to cause movement thereof. It is contemplated that distal end 835 may be fixedly mounted with back frame 814 to facilitate movement. It is further contemplated that distal end 835 may be releasably engageable with back frame 814.

Back frame 814 includes a panel bracket 816 for mounting a user contact pad 818 thereto. Panel bracket 816 is fixedly mounted with back frame 814. It is envisioned that panel bracket 816 may be pivotably mounted to back frame 814 to facilitate pivotal movement of contact pad 818 with a user during use. It is envisioned that contact pad 818 may be variously sized to support various body parts and sizes.

Fitness device 810 may be employed for various stretching treatment such as proprioceptive neuromuscular facilitation stretching, hamstring/hip flexor stretch, quadriceps stretch, iliopsoas stretch, adductor stretch, groin stretch, etc. The advantageous configuration of fitness device 810 provides several advantages including enhanced muscular strength of a user, resilience and increasing a user's joint range of motion.

INDUSTRIAL APPLICABILITY

The present invention is particularly suitable for application to modern industrial processes. In particular, the present invention is constructed of common materials, such as aluminum tubing, and can be easily manufactured using conventional techniques, such as metal bending. The inventive fitness device may be constructed of a less durable, more lightweight materials, such as utilizing a lighter thinner gage of aluminum tubing for the frame, and a thinner plywood substrate for the contacting surfaces. This construction may be suitable for home use. On the other hand, a more robust construction, suitable for commercial fitness club use may utilize, for example heavier gage steel or aluminum tubing for the frame, and a thicker plywood substrate for the contacting surfaces. Similarly, the other components of the inventive fitness device may be selectively chosen depending on the intended use, and the durability, compactness and weight considerations thereof.

While an illustrative embodiment of the invention has been described above, it is, of course, understood that various modifications will be apparent to those of ordinary skill in the art. Such modifications are within the spirit and scope of the invention, which is limited and defined only by the appended claims.

The invention claimed is:

1. A fitness device for use by a person, comprising:
   a) a first contacting member defining a first plane;
   b) a pivotable connecting member attached to said first contacting member;
   c) a mounting bracket connected to said pivotable connecting member in a configuration to facilitate pivotal movement of said first contacting and pivotable connecting members about an axis,
   d) a rigid second contacting member, said mounting bracket further being configured for removable attachment to said second contacting member, defining a second plane with respect to said first contacting member and said first plane, each of said contacting members being suitable for contacting the torso or legs of a user; and
   e) at least one drive mechanism attached to said mounting bracket, said pivotable connecting member having a concave arcuate curvature when attached to said second contacting member in relation to said second contacting member such that operation of said drive mechanism engages said pivotable connecting member and causes said pivotable connecting member to pivot about said axis and adjust the relative positions of said first and second planes to define angles between said planes adjustable from substantially less than 90° to angles substantially greater than 90° and fixes said angles at selected desired angles and substantially maintains said selected desired angles against any forces applied by a user that tend to increase said desired selected angles, said first contacting and pivotable connecting members, said mounting bracket, and said drive mechanism forming a kit or assembly that can be selectively attached or detached to said second contacting member, whereby said kit or assembly can be transported without said second contacting member and attached to any available second contacting member for use as a fitness device.

2. A fitness device according to claim 1, wherein said axis is closely aligned with a hip of a user.

3. A fitness device according to claim 1, wherein said drive mechanism is affixed to said second contacting member by means of a drive mounting member that attaches to said existing second contacting member.

4. A fitness device according to claim 1, wherein said drive mechanism includes a moveable drive shaft that extends to engage said pivotable connecting means in a configuration that facilitates movement of said pivotable connecting means.

5. A fitness device according to claim 1, wherein said first contacting member comprises a pivotable panel.

6. A fitness device as in claim 2, wherein said axis is below said second contacting member.

7. A fitness device as in claim 6, wherein said pivotal connecting member extends, at a vertical user back position, downwardly from said axis and then upwardly, and then forwardly toward the back of a user.

8. A fitness device as in claim 1, wherein said first and second contacting members are spaced at a distance from each other sufficient for a user to extend at least one leg there between for positioning the user's at least one leg either prior to or during use of the device.

9. A fitness device as in claim 1, wherein said second contacting member comprises a table or similarly configured structure.

* * * * *